(12) United States Patent
Sambilay, Jr. et al.

(10) Patent No.: US 10,627,798 B2
(45) Date of Patent: Apr. 21, 2020

(54) FPGA FUNCTIONALITY MODE SWITCH-OVER

(71) Applicant: NVXL Technology, Inc., Fremont, CA (US)

(72) Inventors: Federico Sambilay, Jr., Fremont, CA (US); Bharadwaj Pudipeddi, San Jose, CA (US); Richard A. Cantong, Fremont, CA (US); Joevanni Parairo, Fremont, CA (US)

(73) Assignee: BiTMICRO Networks, Inc., Fremont, CA (US)

( * ) Notice: Subject to any disclaimer, the term of this patent is extended or adjusted under 35 U.S.C. 154(b) by 0 days.

(21) Appl. No.: 16/024,730

(22) Filed: Jun. 29, 2018

(65) Prior Publication Data

US 2019/0018386 A1 Jan. 17, 2019

Related U.S. Application Data

(60) Provisional application No. 62/526,477, filed on Jun. 29, 2017.

(51) Int. Cl.
*G05B 19/05* (2006.01)
*H03K 19/177* (2020.01)
(Continued)

(52) U.S. Cl.
CPC .......... *G05B 19/05* (2013.01); *A61B 5/6869* (2013.01); *G05B 19/042* (2013.01);
(Continued)

(58) Field of Classification Search
None
See application file for complete search history.

(56) References Cited

U.S. PATENT DOCUMENTS 6,326,806 B1 * 12/2001 Fallside .............. G06F 15/7867
326/38
6,573,748 B1 * 6/2003 Trimberger ...... H03K 19/17744
326/38

(Continued)

*Primary Examiner* — Minh D A
*Assistant Examiner* — James H Cho

(57) ABSTRACT

In an embodiment of the invention, an apparatus comprises: a non-volatile memory device; a complex programmable logic device (CPLD) coupled to the non-volatile memory device; a field programmable gate array (FPGA) coupled to the CPLD; and a host coupled to the FPGA; wherein the apparatus triggers a switch of an FPGA image in the FPGA to another FPGA image. In another embodiment of the invention, a method comprises: triggering, by an apparatus, a switch of an FPGA image in a field programmable gate array (FPGA) to another FPGA image; herein the apparatus comprises: a non-volatile memory device; a complex programmable logic device (CPLD) coupled to the non-volatile memory device; the field programmable gate array (FPGA) coupled to the CPLD; and a host coupled to the FPGA. In yet another embodiment of the invention, an article of manufacture comprises a non-transitory computer-readable medium having stored thereon instructions operable to permit an apparatus to perform a method comprising: triggering, by the apparatus, a switch of an FPGA image in a field programmable gate array (FPGA) to another FPGA image, wherein the apparatus comprises: a non-volatile memory device; a complex programmable logic device (CPLD) coupled to the non-volatile memory device; the field programmable gate array (FPGA) coupled to the CPLD; and a host coupled to the FPGA.

27 Claims, 4 Drawing Sheets

(51) Int. Cl.
*A61B 5/00* (2006.01)
*G06F 17/50* (2006.01)
*G05B 19/042* (2006.01)
*A61B 5/024* (2006.01)
*H03K 19/1776* (2020.01)

(52) U.S. Cl.
CPC ..... *G06F 17/5054* (2013.01); *H03K 19/1776* (2013.01); *A61B 5/024* (2013.01); *G05B 2219/34024* (2013.01)

(56) References Cited

U.S. PATENT DOCUMENTS 7,685,380 B1 * 3/2010 Khu .................... G06F 12/0246
 711/102
8,896,346 B1 * 11/2014 Lewis ................. H03K 19/177
 326/41

* cited by examiner

FPGA FUNCTIONALITY MODE SWITCH-OVER

CROSS-REFERENCE(S) TO RELATED APPLICATION

This application claims the benefit of and priority to U.S. Provisional Application No. 62/526,477 which was filed on Jun. 29, 2017. This U.S. Provisional Application No. 62/526,477 is hereby fully incorporated herein by reference.

FIELD

Embodiments of the invention relate generally the field of field programmable field arrays (FPGAs), and relate particularly to the use of a FPGA device in the environment that requires FPGA re-configuration.

DESCRIPTION OF RELATED ART

The background description provided herein is for the purpose of generally presenting the context of the disclosure of the invention. Work of the presently named inventors, to the extent the work is described in this background section, as well as aspects of the description that may not otherwise qualify as prior art at the time of filing, are neither expressly nor impliedly admitted as prior art against this present disclosure of the invention.

FPGA re-configuration is performed by various methods. However, there is a continuing need to overcome the constraints and/or disadvantages of conventional approaches.

SUMMARY

Embodiments of the invention relate generally the field of field programmable field arrays (FPGAs), and relate particularly to the use of a FPGA device in the environment that requires FPGA re-configuration.

In an embodiment of the invention, an apparatus comprises: a non-volatile memory device; a complex programmable logic device (CPLD) coupled to the non-volatile memory device; a field programmable gate array (FPGA) coupled to the CPLD; and a host coupled to the FPGA; wherein the apparatus triggers a switch of an FPGA image in the FPGA to another FPGA image.

In another embodiment of the invention, a method comprises: triggering, by an apparatus, a switch of an FPGA image in a field programmable gate array (FPGA) to another FPGA image; herein the apparatus comprises: a non-volatile memory device; a complex programmable logic device (CPLD) coupled to the non-volatile memory device; the field programmable gate array (FPGA) coupled to the CPLD; and a host coupled to the FPGA.

In yet another embodiment of the invention, an article of manufacture comprises a non-transitory computer-readable medium having stored thereon instructions operable to permit an apparatus to perform a method comprising: triggering, by the apparatus, a switch of an FPGA image in a field programmable gate array (FPGA) to another FPGA image, wherein the apparatus comprises: a non-volatile memory device; a complex programmable logic device (CPLD) coupled to the non-volatile memory device; the field programmable gate array (FPGA) coupled to the CPLD; and a host coupled to the FPGA.

It is to be understood that both the foregoing general description and the following detailed description are exemplary and explanatory only and are not restrictive of the invention, as claimed. For example, the foregoing general description presents a simplified summary in order to provide a basic understanding of some aspects described herein. This summary is not an extensive overview of the claimed subject matter. This summary is intended to neither identify key or critical elements of the claimed subject matter nor delineate the scope thereof. The sole purpose of the summary is to present some concepts in a simplified form as a prelude to the more detailed description that is presented later.

The accompanying drawings, which are incorporated in and constitute a part of this specification, illustrate one (several) embodiment(s) of the invention and together with the description, serve to explain the principles of the invention.

BRIEF DESCRIPTION OF THE DRAWINGS

Non-limiting and non-exhaustive embodiments of the present invention are described with reference to the following figures, wherein like reference numerals refer to like parts throughout the various views unless otherwise specified.

It is to be noted, however, that the appended drawings illustrate only typical embodiments of this invention and are therefore not to be considered limiting of its scope, for the present invention may admit to other equally effective embodiments.

DETAILED DESCRIPTION

Figure 1:
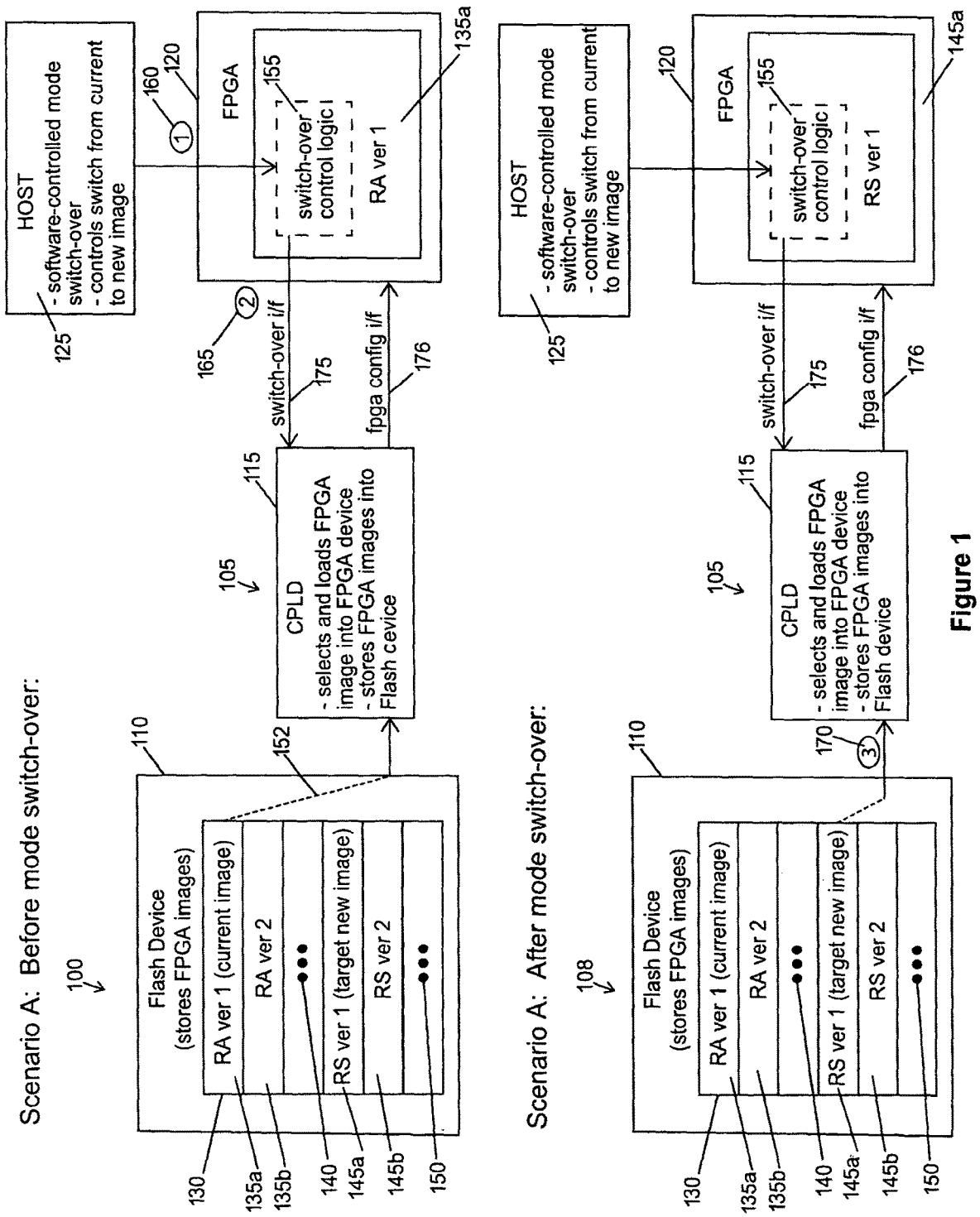
FIG. 1 is a block diagram of a first scenario, in accordance with an embodiment of the invention.

In the following detailed description, for purposes of explanation, numerous specific details are set forth to provide a thorough understanding of the various embodiments of the present invention. Those of ordinary skill in the art will realize that these various embodiments of the present invention are illustrative only and are not intended to be limiting in any way. Other embodiments of the present invention will readily suggest themselves to such skilled persons having the benefit of this disclosure.

In addition, for clarity purposes, not all of the routine features of the embodiments described herein are shown or described. One of ordinary skill in the art would readily appreciate that in the development of any such actual implementation, numerous implementation-specific decisions may be required to achieve specific design objectives. These design objectives will vary from one implementation to another and from one developer to another. Moreover, it will be appreciated that such a development effort might be complex and time-consuming, but would nevertheless be a routine engineering undertaking for those of ordinary skill in the art having the benefit of this disclosure. The various embodiments disclosed herein are not intended to limit the scope and spirit of the herein disclosure.

Exemplary embodiments for carrying out the principles of the present invention are described herein with reference to the drawings. However, the present invention is not limited to the specifically described and illustrated embodiments. A person skilled in the art will appreciate that many other embodiments are possible without deviating from the basic concept of the invention. Therefore, the principles of the present invention extend to any work that falls within the scope of the appended claims.

As used herein, the terms "a" and "an" herein do not denote a limitation of quantity, but rather denote the presence of at least one of the referenced items.

In the following description and in the claims, the terms "include" and "comprise" are used in an open-ended fashion, and thus should be interpreted to mean "include, but not limited to . . . ". Also, the term "couple" (or "coupled") is intended to mean either an indirect or direct electrical connection (or an indirect or direct optical connection). Accordingly, if one device is coupled to another device, then that connection may be through a direct electrical (or optical) connection, or through an indirect electrical (or optical) connection via other devices and/or other connections.

An embodiment of this invention presents a mechanism that can be used in a system with a FPGA (field programmable gate array) device, a CPLD (or any equivalent device used for the same purpose), and a flash device (i.e., flash memory device or any device used for the same purpose or any suitable non-volatile memory device). Multiple FPGA images are stored in the flash device. The CPLD (complex programmable logic device) is used to store and select which FPGA image to load into the FPGA. An embodiment of this invention presents a mechanism where the system can select which FPGA image can be loaded into the FPGA device. The following are the example scenarios where the invention is used.

(1) Scenario A: Host-controlled manual selection of which FPGA image to load, (2) Scenario B: FPGA auto-configuration when a current FPGA image is corrupted, and/or (3) Scenario C: FPGA auto-configuration when a current FPGA image is partially working, but a connection to the host is gone or has failed.

As known to those skilled in the art, a given FPGA image as discussed herein (e.g., RA version 1, RA version 2, RS version 1, RS version 2, current FPGA image, or default FPGA image) permits an FPGA (e.g., FPGA 120, FPGA 220, or FPGA 320) to perform a given FPGA functionality (or given FPGA functionality mode) or given FPGA functionalities (or given FPGA functionality modes).

FIG. 1 is a block diagram 100 of a first scenario (Scenario A) before an FPGA functionality mode switch-over of an apparatus 105, in accordance with an embodiment of the invention. FIG. 1 also shows a block diagram 108 of the first scenario (scenario A) after an FPGA functionality mode switch-over of the apparatus 105, in accordance with an embodiment of the invention. Scenario A involves a host-controlled manual selection (as performed by a host) of which FPGA image to load into an FPGA device.

In an embodiment of the invention, the apparatus 105 comprises a flash device 110, a CPLD 115, a FPGA 120, and a host 125. The flash device 110 is communicatively coupled to and/or electrically coupled to the CPLD 115. The CPLD 115 is communicatively coupled to and/or electrically coupled to the FPGA 120. The host 125 is communicatively coupled to and/or electrically coupled to the FPGA 120.

The flash device 110 stores FPGA images 130. For example, the FPGA images 130 comprises RA version 1 (135a) which is the current image in the FPGA 120 and RA version 2 (135b) which is another version of the current image in the FPGA 120. The number of versions of the current image in the FPGA 120 may vary as symbolically shown by the dot symbols 140.

The FPGA images 130 also comprises RS version 1 (145a) which is the target new image for the FPGA 120 and RS version 2 (145b) which is another version of the target new image for the FPGA 120. The number of versions of the target new image for the FPGA 120 may vary as symbolically shown by the dot symbols 150.

The CPLD 115 selects and loads an FPGA image into the FPGA device 120. The CPLD 115 stores FPGA images into the flash device 110.

The FPGA 120 currently stores RA version 1 (135a) which is the current FPGA image in diagram 100. The CPLD 115 previously selected (152) and previously loaded (152) the current image 135a into the FPGA 120.

The host 125 can be, for example, a central processing unit (CPU), a server or another type of computer, or another type of host device. The host 125 provides a software-control mode switch-over for providing a FPGA functionality mode switch-over so that the host 125 provides a host-controlled manual selection of which FPGA image to load into the FPGA 120 from the flash device 110. The host 125 controls the switching from the current image 135a in the FPGA 120 to a target new image 145a in the FPGA 120.

The FPGA 120 comprises a switch-over control logic 155 that switches the current image 135a in the FPGA 120 to a target new image 145a in the FPGA 120.

The scenario A steps are as follows.

In step 1 (160), the host 125 triggers a switch from the current image (RA) 135a to a target new image (RS) 145a.

In step 2 (165), the switch-over control logic 155 inside the FPGA 120 tells the CPLD 155 to load a new target image 145a.

In step 3 (170), the CPLD 115 selects and loads the target new image 145a into the FPGA 120.

The switch-over control logic 155 is communicatively coupled to and/or electrically coupled to the CPLD 115 by the switch-over interface 175. The CPLD 115 is communicatively coupled to and/or electrically coupled to the FPGA 120 by the FPGA configuration interface 176. The FPGA configuration interface 176 is also shown in FIGS. 2 and 3.

The scenario A after the FPGA functionality mode switch-over is shown in diagram 108. In diagram 108, the target image 145a has been loaded into the FPGA 120.

Figure 2:
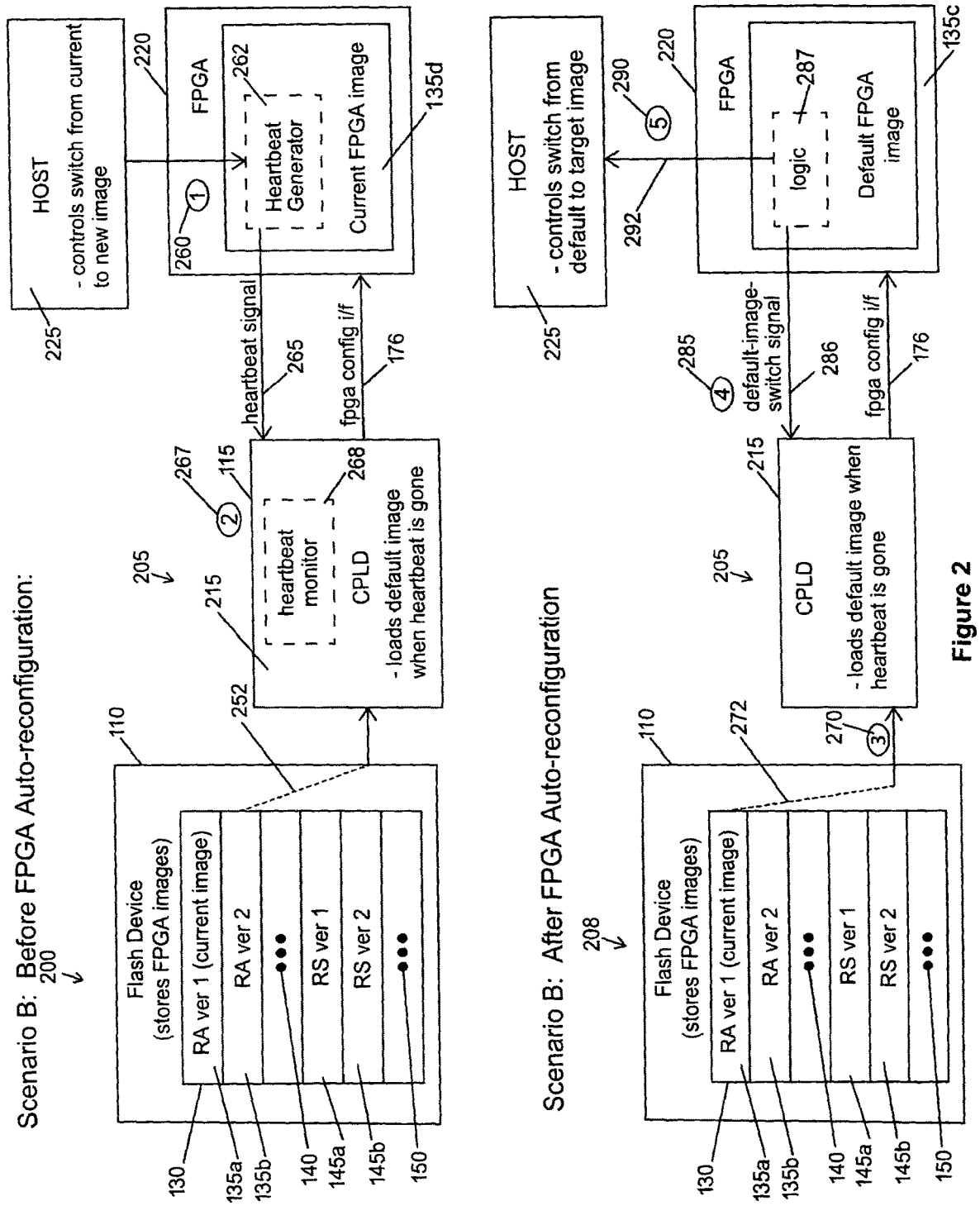
FIG. 2 is a block diagram of a second scenario, in accordance with an embodiment of the invention.
Figure 3:
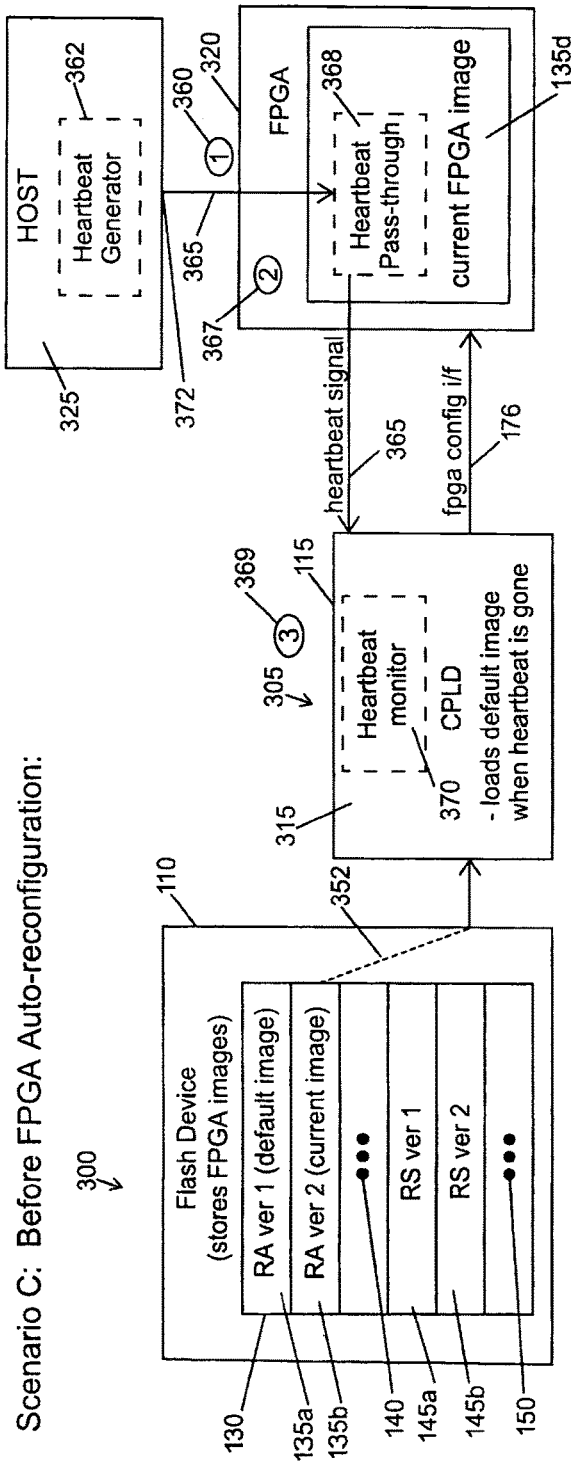
FIG. 3 is a block diagram of a third scenario, in accordance with an embodiment of the invention.

FIG. 2 is a block diagram 200 of a second scenario (Scenario B) before an FPGA auto-configuration when the current FPGA image is corrupted in an apparatus 205, in accordance with an embodiment of the invention. FIG. 2 also shows a block diagram 208 of the second scenario (Scenario B) after the FPGA auto-reconfiguration of the apparatus 205, in accordance with an embodiment of the invention. Scenario B involves an FPGA auto-reconfiguration when the current FPGA image in an FPGA (e.g., FPGA 220) is corrupted.

In an embodiment of the invention, the apparatus 205 comprises a flash device 110, a CPLD 215, a FPGA 220, and a host 225. Features and/or functions of the flash device 110, CPLD 215, FPGA 220, and host 225 have been similarly discussed with reference to the flash device 110, CPLD 115, FPGA 120, and host 125, respectively, in FIG. 1. Additional features and/or functions of the flash device 110, CPLD 215, FPGA 220, and host 225 are also discussed below.

The flash device 110 is communicatively coupled to and/or electrically coupled to the CPLD 215. The CPLD 215 is communicatively coupled to and/or electrically coupled to the FPGA 220. The host 225 is communicatively coupled to and/or electrically coupled to the FPGA 220.

The flash device 110 stores FPGA images 130. For example, the FPGA images 130 comprises RA version 1 (135c) which is the default FPGA image in the FPGA 220 and RA version 2 (135d) which is the current FPGA image in the FPGA 220. The number of versions of the current FPGA image in the FPGA 120 may vary as symbolically shown by the dot symbols 140.

The FPGA images 130 also comprises RS version 1 (145a) which is the target new image for the FPGA 120 and RS version 2 (145b) which is another version of the target new image for the FPGA 120. The number of versions of the target new image for the FPGA 120 may vary as symbolically shown by the dot symbols 150.

The FPGA 220 currently stores RA version 2 (current FPGA image) 135d in diagram 200. The CPLD 215 previously selected (252) and previously loaded (252) the current FPGA image 135d into the FPGA 220.

The host 225 controls the switching from the current FPGA image 135d in the FPGA 220 to a target new image 145a in the FPGA 220.

The CPLD 215 loads a default FPGA image 135c when a heartbeat signal 265 from the heartbeat generator 262 is gone.

The scenario B steps are as follows.

In step 1 (260), a heartbeat generator 262 (in FPGA 220) continuously generates a heartbeat signal 265, with the heartbeat generator 262 sending the heartbeat signals 265 to the CPLD 215.

In step 2 (267), the heartbeat monitor 268 (in CPLD 215) monitors the heartbeat signal 265 from the FPGA device 220. When the current FPGA image 135d is corrupted, the heartbeat generator 262 stops the generation of the heartbeat signal 265.

In step 3 (270), the heartbeat monitor 268 detects that the heartbeat signal 265 from the FPGA 220 is gone. In step 3 (270), the CPLD 215 loads (272) the default image 135c into the FPGA 220.

In step 4 (285), the CPLD 215 sends a default image switch signal 286 to a logic 287 in the new FPGA image 135c. The signal 286 indicates that a switch to the default FPGA image 135c has happened in the FPGA 220.

In step 5 (290), a report 292 is sent by the logic 287 to the Host 125. The report 292 indicates to the host 225 that a switch to the default FPGA image 135c has happened in the FPGA 220. The host 125 can then initiate the switch to the new target FPGA image 145a into the FPGA 220.

FIG. 3 is a block diagram 300 of a third scenario (Scenario C) before an FPGA auto-reconfiguration of an apparatus 305, in accordance with an embodiment of the invention. FIG. 3 also shows a block diagram 308 of the third scenario (Scenario C) after the FPGA auto-reconfiguration of the apparatus 305, in accordance with an embodiment of the invention. Scenario C involves a FPGA auto-configuration when the current FPGA image in the FPGA is partially working, but a connection to the host is gone or has failed.

In an embodiment of the invention, the apparatus 305 comprises a flash device 110, a CPLD 315, a FPGA 320, and a host 325. Features and/or functions of the flash device 110, CPLD 315, FPGA 320, and host 325 have been similarly discussed with reference to the flash device 110, CPLD 115, FPGA 120, and host 125, respectively, in FIG. 1. The flash device 110 is communicatively coupled to and/or electrically coupled to the CPLD 315. The CPLD 315 is communicatively coupled to and/or electrically coupled to the FPGA 320. The host 325 is communicatively coupled to and/or electrically coupled to the FPGA 320.

The flash device 110 stores FPGA images 130. For example, the FPGA images 130 comprises RA version 1 (135c) which is the default FPGA image in the FPGA 320 and RA version 2 (135d) which is the current FPGA image in the FPGA 320. The number of versions of the current FPGA image in the FPGA 320 may vary as symbolically shown by the dot symbols 140.

The FPGA images 130 also comprises RS version 1 (145a) which is the target new image for the FPGA 320 and RS version 2 (145b) which is another version of the target new image for the FPGA 320. The number of versions of the target new image for the FPGA 320 may vary as symbolically shown by the dot symbols 150.

The CPLD 315 loads a default FPGA image 135c into the FPGA 320 with the heartbeat signal from the heartbeat generator in the host 325 is gone.

The FPGA 320 currently stores RA version 2 (current FPGA image) 135d in diagram 300. The CPLD 115 previously selected (352) and previously loaded (352) the current image 135a into the FPGA 320.

The host 325 controls the switching from the default image in the FPGA 320 to a target image 145a in the FPGA 320.

The Scenario C steps are as follows.

In step 1 (360), a heartbeat generator 362 in the host side (i.e., host 325) continuously generates heartbeat signal 365, and the heartbeat generator 362 sends the heartbeat signals 365 to the FPGA device 320.

In step 2 (367), the FPGA device 320 passes the heartbeat signal 365 to the CPLD 315. The FPGA device 320 comprises a heartbeat pass-through logic 368 that passes the heartbeat signal 365 from the host 325 to the CPLD 315.

In step 3 (369), the heartbeat monitor 370 (in CPLD 315) monitors the heartbeat signal 365 from the FPGA device 320. When the current FPGA image 135d is partially working, but a host connection 372 (e.g., PCIe link or Peripheral Component Interconnect Express link) is gone or becomes defective, the heartbeat signal 365 from the host 325 is not received by the FPGA 320.

In step 4 (375), the heartbeat monitor 370 detects that the heartbeat signal 365 from the FPGA 320 is gone. The CPLD 315 loads (377) the default image 135c into the FPGA 320.

In step 5 (380), the CPLD 315 sends a default image switch signal 382 to a logic 384 in the new FPGA image 135c. The signal 382 indicates that a switch to the default FPGA image 135c has happened in the FPGA 320.

In step 6 (385), a report 386 is sent form the logic 384 to the Host 325 that a switch to the default FPGA image 135c has happened in the FPGA 320. The Host 325 can then initiate the switch to the new target FPGA image 145a in the FPGA 320.

Figure 4:
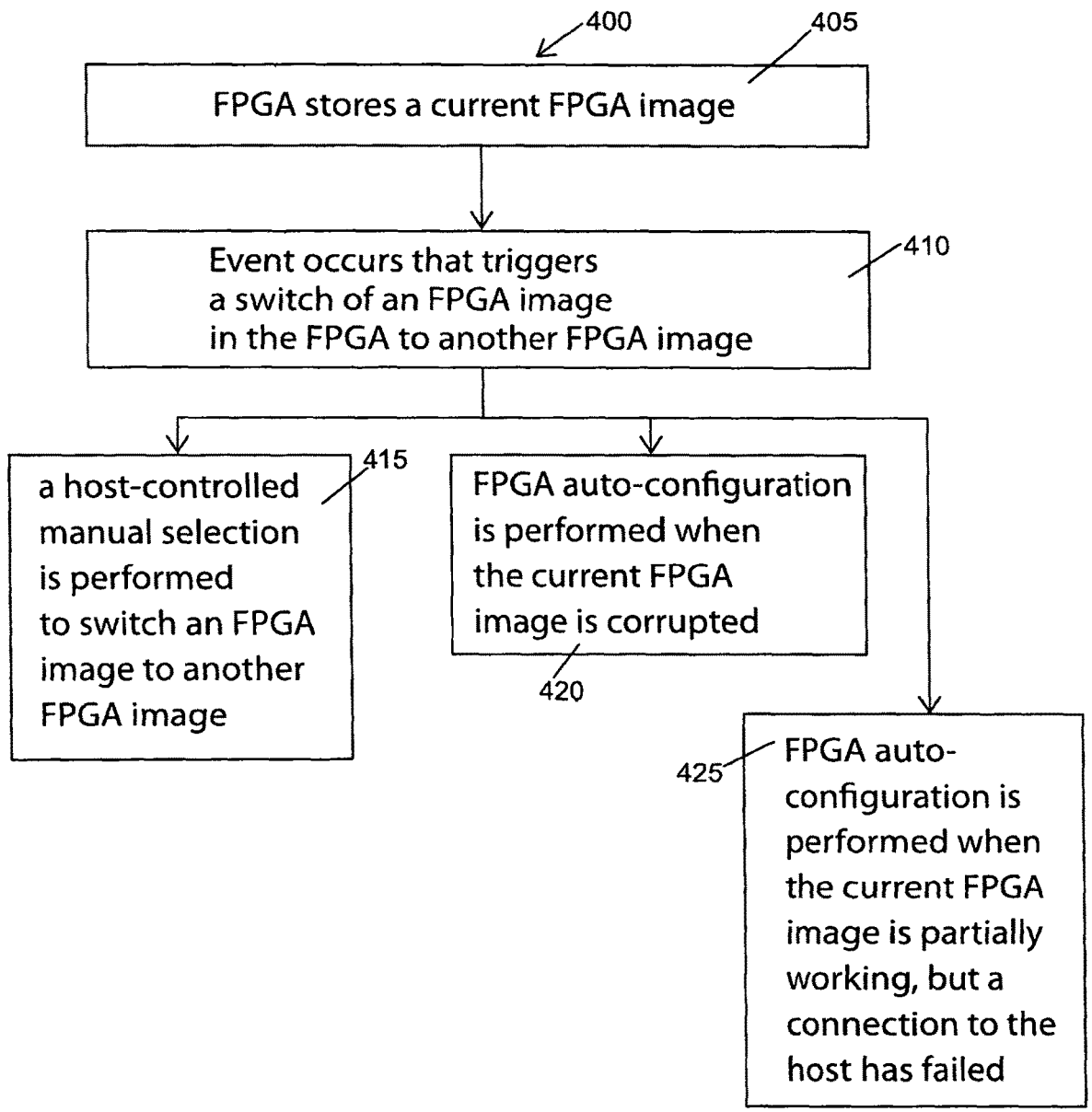
FIG. 4 is a flow diagram of a method, in accordance with an embodiment of the invention.

FIG. 4 is a flow diagram of a method 400, in accordance with an embodiment of the invention.

At 405, an FPGA stores a current FPGA image.

At 410, an event occurs that triggers a switch of an FPGA image in the FPGA to another FPGA image.

The event 410 may be a host-controlled manual selection. At 415, a host-controlled manual selection is performed to switch an FPGA image (in the FPGA) to another FPGA image.

The event 410 may be a current FPGA image (in the FPGA) become corrupted. At 420, an FPGA auto-configuration is performed when the current FPGA image (in the FPGA) is corrupted.

The event 410 may be a connection to a host as subject to failure. At 425, an FPGA auto-configuration is performed when the current FPGA image (in the FPGA) is partially working, but a connection to the host has failed, wherein the host is communicatively coupled to and/or electrically coupled to the FPGA.

Embodiments of the invention relate generally the field of field programmable field arrays (FPGAs), and relate particularly to the use of a FPGA device in the environment that requires FPGA re-configuration.

In an embodiment of the invention, an apparatus comprises: a non-volatile memory device; a complex programmable logic device (CPLD) coupled to the non-volatile memory device; a field programmable gate array (FPGA) coupled to the CPLD; and a host coupled to the FPGA; wherein the apparatus triggers a switch of an FPGA image in the FPGA to another FPGA image.

In another embodiment of the invention, a method comprises: triggering, by an apparatus, a switch of an FPGA image in a field programmable gate array (FPGA) to another FPGA image; herein the apparatus comprises: a non-volatile memory device; a complex programmable logic device (CPLD) coupled to the non-volatile memory device; the field programmable gate array (FPGA) coupled to the CPLD; and a host coupled to the FPGA.

In yet another embodiment of the invention, an article of manufacture comprises a non-transitory computer-readable medium having stored thereon instructions operable to permit an apparatus to perform a method comprising: triggering, by the apparatus, a switch of an FPGA image in a field programmable gate array (FPGA) to another FPGA image, wherein the apparatus comprises: a non-volatile memory device; a complex programmable logic device (CPLD) coupled to the non-volatile memory device; the field programmable gate array (FPGA) coupled to the CPLD; and a host coupled to the FPGA.

The word "exemplary" (or "example") is used herein to mean serving as an example, instance, or illustration. Any aspect or embodiment or design described herein as "exemplary" or "example" is not necessarily to be construed as preferred or advantageous over other aspects or embodiments or designs. Similarly, examples are provided herein solely for purposes of clarity and understanding and are not meant to limit the subject innovation or portion thereof in any manner. It is to be appreciated that a myriad of additional or alternate examples could have been presented, but have been omitted for purposes of brevity and/or for purposes of focusing on the details of the subject innovation.

As used in herein, the terms "component", "system", "module", "element", and/or the like are intended to refer to a computer-related entity, either hardware, a combination of hardware and software, software, or software in execution. For example, a component or element may be, but is not limited to being, a process running on a processor, a processor, an object, an instance, an executable, a thread of execution, a program, and/or a computer. By way of example, both an application running on a computer and the computer can be a component. One or more components may reside within a process and/or thread of execution and a component may be localized on one computer and/or distributed between two or more computers.

Foregoing described embodiments of the invention are provided as illustrations and descriptions. They are not intended to limit the invention to precise form described. In particular, it is contemplated that functional implementation of invention described herein may be implemented equivalently in hardware, software, firmware, and/or other available functional components or building blocks, and that networks may be wired, wireless, or a combination of wired and wireless.

It is also within the scope of the present invention to implement a program or code that can be stored in a non-transient machine-readable medium (or non-transitory machine-readable medium or non-transient computer-readable medium or non-transitory computer-readable medium) having stored thereon instructions that permit a method (or that permit a computer) to perform any of the inventive techniques described above, or a program or code that can be stored in an article of manufacture that includes a non-transient computer readable medium (non-transitory computer readable medium) on which computer-readable instructions for carrying out embodiments of the inventive techniques are stored. Other variations and modifications of the above-described embodiments and methods are possible in light of the teaching discussed herein.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined entirely by the following claims, which are to be construed in accordance with established doctrines of claim interpretation.

What is claimed is:

1. An apparatus, comprising:
a non-volatile memory device;
a complex programmable logic device (CPLD) coupled to the non-volatile memory device;
a field programmable gate array (FPGA) coupled to the CPLD; and
a host coupled to the FPGA;
wherein the apparatus triggers a switch of an FPGA image in the FPGA to another FPGA image and the FPGA comprises a heartbeat generator that sends a heartbeat signal to the CPLD and stops sending the heartbeat signal if the FPGA image is corrupted.

2. The apparatus of claim 1, wherein the host triggers the switch from the FPGA image to the another FPGA image.

3. The apparatus of claim 1, wherein the CPLD selects the another image from the non-volatile memory device and loads the another FPGA image into the FPGA.

4. The apparatus of claim 3, wherein the CPLD comprises a heartbeat monitor that monitors heartbeat signals.

5. The apparatus of claim 4, wherein the CPLD loads a default FPGA image into the FPGA in response to the heartbeat monitor failing to detect heartbeat signals.

6. The apparatus of claim 5, wherein the FPGA sends a report to the host in response to the default FPGA image being loaded into the FPGA and wherein the host switches the default FPGA image in the FPGA to the another FPGA image.

7. The apparatus of claim 3, wherein the CPLD loads a default FPGA image into the FPGA in response to the FPGA image becoming corrupted.

8. The apparatus of claim 7, wherein the FPGA sends a report to the host in response to the default FPGA image being loaded into the FPGA and wherein the host switches the default FPGA image in the FPGA to the another FPGA image.

9. The apparatus of claim 1, wherein the host comprises a heartbeat generator that sends a heartbeat signal to the FPGA, wherein the FPGA comprises a heartbeat pass-through logic for passing the heartbeat signal from the host to the CPLD, and wherein the heartbeat generator stops sending the heartbeat signal if a host connection to the host has failed.

10. A method, comprising:
triggering, by an apparatus, a switch of an FPGA image in a field programmable gate array (FPGA) to another FPGA image;
wherein the apparatus comprises:
a non-volatile memory device;
a complex programmable logic device (CPLD) coupled to the non-volatile memory device;
the field programmable gate array (FPGA) coupled to the CPLD, wherein the FPGA comprises a heartbeat generator that sends a heartbeat signal to the CPLD and stops sending the heartbeat signal if the FPGA image is corrupted; and
a host coupled to the FPGA.

11. The method of claim 10, wherein the host triggers the switch from the FPGA image to the another FPGA image.

12. The method of claim 10, wherein the CPLD selects the another image from the non-volatile memory device and loads the another FPGA image into the FPGA.

13. The method of claim 10, wherein the CPLD comprises a heartbeat monitor that monitors heartbeat signals.

14. The method of claim 13, wherein the CPLD loads a default FPGA image into the FPGA in response to the FPGA image becoming corrupted.

15. The method of claim 14, wherein the FPGA sends a report to the host in response to the default FPGA image being loaded into the FPGA and wherein the host switches the default FPGA image in the FPGA to the another FPGA image.

16. The method of claim 14, wherein the CPLD loads a default FPGA image into the FPGA in response to the heartbeat monitor failing to detect heartbeat signals.

17. The method of claim 16, wherein the FPGA sends a report to the host in response to the default FPGA image being loaded into the FPGA and wherein the host switches the default FPGA image in the FPGA to the another FPGA image.

18. The method of claim 10, wherein the host comprises a heartbeat generator that sends a heartbeat signal to the FPGA, wherein the FPGA comprises a heartbeat pass-through logic for passing the heartbeat signal from the host to the CPLD, and wherein the heartbeat generator stops sending the heartbeat signal if a host connection to the host has failed.

19. An article of manufacture, comprising:
a non-transitory computer-readable medium having stored thereon instructions operable to permit an apparatus to perform a method comprising:
triggering, by the apparatus, a switch of an FPGA image in a field programmable gate array (FPGA) to another FPGA image;
wherein the apparatus comprises:
a non-volatile memory device;
a complex programmable logic device (CPLD) coupled to the non-volatile memory device;
the field programmable gate array (FPGA) coupled to the CPLD, wherein the FPGA comprises a heartbeat generator that sends a heartbeat signal to the CPLD and stops sending the heartbeat signal if the FPGA image is corrupted; and
a host coupled to the FPGA.

20. The article of manufacture of claim 19, wherein the host triggers the switch from the FPGA image to the another FPGA image.

21. The article of manufacture of claim 19, wherein the CPLD selects the another image from the non-volatile memory device and loads the another FPGA image into the FPGA.

22. The article of manufacture of claim 19, wherein the CPLD comprises a heartbeat monitor that monitors heartbeat signals.

23. The article of manufacture of claim 22, wherein the CPLD loads a default FPGA image into the FPGA in response to the heartbeat monitor failing to detect heartbeat signals.

24. The article of manufacture of claim 23, wherein the FPGA sends a report to the host in response to the default FPGA image being loaded into the FPGA and wherein the host switches the default FPGA image in the FPGA to the another FPGA image.

25. The article of manufacture of claim 19, wherein the CPLD loads a default FPGA image into the FPGA in response to the FPGA image becoming corrupted.

26. The article of manufacture of claim 25, wherein the FPGA sends a report to the host in response to the default FPGA image being loaded into the FPGA and wherein the host switches the default FPGA image in the FPGA to the another FPGA image.

27. The article of manufacture of claim 19, wherein the host comprises a heartbeat generator that sends a heartbeat signal to the FPGA, wherein the FPGA comprises a heartbeat pass-through logic for passing the heartbeat signal from the host to the CPLD, and wherein the heartbeat generator stops sending the heartbeat signal if a host connection to the host has failed.

* * * * *